(12) United States Patent
Ross

(10) Patent No.: US 8,257,337 B2
(45) Date of Patent: Sep. 4, 2012

(54) INTRAVENOUS FLUID CONTAINER

(75) Inventor: Graham Ross, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 721 days.

(21) Appl. No.: 11/969,044

(22) Filed: Jan. 3, 2008

(65) Prior Publication Data

US 2008/0275422 A1    Nov. 6, 2008

Related U.S. Application Data

(60) Provisional application No. 60/915,627, filed on May 2, 2007.

(51) Int. Cl.
*A61B 19/00* (2006.01)
*G06F 13/42* (2006.01)
*G05B 19/00* (2006.01)

(52) U.S. Cl. ......... 604/408; 604/403; 604/415; 340/1.1; 340/5.8

(58) Field of Classification Search .................. 604/403, 604/408, 415
See application file for complete search history.

(56) References Cited

U.S. PATENT DOCUMENTS

| | | | | |
|---|---|---|---|---|
| 4,641,362 A * | 2/1987 | Muller | .......................... | 383/115 |
| 4,645,486 A * | 2/1987 | Beal et al. | .................... | 604/4.01 |
| 4,675,019 A * | 6/1987 | Bellhouse et al. | ............ | 604/408 |
| 4,869,398 A * | 9/1989 | Colvin et al. | .................... | 222/83 |
| 4,950,245 A * | 8/1990 | Brown et al. | ................. | 604/153 |
| 5,078,683 A | 1/1992 | Sancoff et al. | | |
| 5,090,963 A * | 2/1992 | Gross et al. | .................... | 604/132 |
| 5,317,506 A | 5/1994 | Coutre et al. | | |
| 5,420,962 A * | 5/1995 | Bakke | ........................... | 392/470 |
| 5,562,836 A * | 10/1996 | Joie et al. | ...................... | 210/782 |
| 5,750,216 A * | 5/1998 | Horino et al. | ................ | 428/34.3 |
| 5,873,731 A | 2/1999 | Prendergast | | |
| 6,519,569 B1 * | 2/2003 | White et al. | ...................... | 705/3 |
| 6,620,130 B1 * | 9/2003 | Ginsburg | ...................... | 604/113 |
| 6,663,829 B1 * | 12/2003 | Kjellstrand | ....................... | 422/1 |
| 6,748,332 B2 * | 6/2004 | Chen | ................................. | 702/19 |
| 7,041,941 B2 * | 5/2006 | Faries et al. | .................... | 219/413 |
| 7,083,068 B2 * | 8/2006 | Rake et al. | ..................... | 222/103 |
| 7,236,936 B2 * | 6/2007 | White et al. | ...................... | 705/3 |
| 7,510,546 B2 * | 3/2009 | Baessler et al. | ................ | 604/408 |
| 7,681,606 B2 * | 3/2010 | Khan et al. | ..................... | 141/147 |

(Continued)

FOREIGN PATENT DOCUMENTS

JP    2003225305    8/2003

(Continued)

*Primary Examiner* — Tatyana Zalukaeva
*Assistant Examiner* — Susan Su
(74) *Attorney, Agent, or Firm* — McDermott Will & Emery LLP

(57) ABSTRACT

An IV product comprises a flexible fluid bag and a container housing for supporting and protecting the fluid bag. The IV product may include an information element such as a bar code, RFID or the like which provides information. The IV product may also include a mechanism for expelling fluid from the fluid bag, such as an inflatable bellows. In one embodiment, the IV product may be mated to a docking station or receptacle. One or more elements may be provided for aligning and connecting the IV product to establish a fluid connection with the fluid bag.

17 Claims, 4 Drawing Sheets

U.S. PATENT DOCUMENTS

| | | |
|---|---|---|
| 2003/0072676 A1* | 4/2003 | Fletcher-Haynes et al. .... 422/23 |
| 2004/0051368 A1 | 3/2004 | Caputo et al. |
| 2004/0073177 A1 | 4/2004 | Hickle |
| 2004/0150525 A1* | 8/2004 | Wilson et al. .............. 340/572.1 |
| 2005/0085786 A1* | 4/2005 | Baessler et al. ............... 604/408 |
| 2005/0209547 A1 | 9/2005 | Burbank et al. |
| 2006/0178619 A1 | 8/2006 | Simpkins |
| 2006/0265186 A1 | 11/2006 | Holland et al. |
| 2008/0215029 A1* | 9/2008 | Rake et al. .................... 604/408 |
| 2009/0036844 A1* | 2/2009 | Fristrup et al. ........... 604/288.04 |
| 2009/0036863 A1* | 2/2009 | Smith et al. ................... 604/408 |

FOREIGN PATENT DOCUMENTS

| | | |
|---|---|---|
| JP | 2006034845 | 2/2006 |

* cited by examiner

INTRAVENOUS FLUID CONTAINER

CROSS-REFERENCE TO RELATED APPLICATIONS

This application claims priority of U.S. Provisional Application No. 60/915,627, titled "Rigid Container for IV Products," filed on May 2, 2007, specifications of which are herein incorporated by reference.

FIELD OF THE INVENTION

The present invention relates to intravenous fluid containers.

BACKGROUND OF THE INVENTION

In the United States, most intravenous fluids are contained in rectangular flexible bags, commonly referred to as intravenous or "IV" bags. These bags are equipped with multiple septum or other fluid connections that allow additional fluids to be added to the bag or which permit connection of the bag to a tube that feeds the fluid to the patient. The bags are floppy and subject to puncture if they come into contact with sharp items. Alternate containers, which may be more prevalent in other countries, include glass bottles and soft plastic bottles.

Administration of these IV fluids, regardless of the container, requires that the fluid container be suspended at some height, typically 0.5-1.0 meter, above the patient or the infusion pump. This container is then connected by a flexible tube to either the patient directly or to an infusion pump. Mounting the fluid container above the delivery point generates a positive pressure due to gravity at the connection of the infusion tube to the patient or pump. One embodiment of such a mounting is illustrated in FIG. 1, wherein an IV bag B is mounted in an elevated position on a pole P. A fluid delivery line L leads from the bag B.

Every step of the processing of such a fluid container has associated risks to the patient, primarily due to the completely manual process of utilizing the container. For example, the IV bag may be incorrectly labeled when additional drugs are added in the pharmacy or other location, leading to a risk that the IV fluid will be administered to the incorrect patient. The bag may also be dropped or mishandled in transit due to the floppy design of the container, leading to either leakage or contamination of the contents or external connections.

SUMMARY OF THE INVENTION

Various aspects of the invention comprise IV products and methods of utilizing such products.

In one embodiment, an IV product comprises a fluid bag and container housing. The fluid bag preferably comprises a flexible member for containing fluid. The fluid bag has at least one fluid connector to permit fluid to be transferred to and from the fluid bag. In one embodiment, the fluid connector may comprise a pierceable septum or other connector to permit a fluid connection to be established.

The container housing preferably comprises a rigid member for protecting and supporting the fluid bag. In one embodiment, the fluid bag and container housing may be separable, while in others they may be integrated. The container housing may completely enclose the fluid bag or only partially enclose the fluid bag, as in the case of a supporting frame.

The IV product may bear one or more information elements. The information element may comprise printed text, such as words, numbers or a bar code, an RFID element or other information. The information may comprise or identify information such as information regarding the IV product (production date, intended use, expiration date, etc.) or the use thereof (intended patient, hospital, etc.).

In one embodiment, the IV product may include mechanism for expelling fluid there from. The mechanism may comprise an inflatable bellows for compressing the fluid bag. The mechanism might comprise other elements or devices, and include a flow sensor, flow stop or other elements.

The IV product may include additional features such as alignment members or elements for mating with external devices such as pumps, docking stations or the like. The IV product may also include mounts or other elements for mounting the IV product, such as for storage in a rack.

In one embodiment, the IV product may be associated with a docking station or other receptacle. In such instance, the IV product may be aligned with and connected to the receptacle. Preferably, at that time a fluid connection is established between a fluid connector of the receptacle or other device and the fluid connector of the fluid bag of the IV product.

The receptacle or other device may include a reader for reading the IV product's information element. The information which is read may be utilized to confirm and control use of the IV product.

Further objects, features, and advantages of the present invention over the prior art will become apparent from the detailed description of the drawings which follows, when considered with the attached figures.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One embodiment of the invention is an IV product comprising a housing for an IV bag or container. This container housing is preferably configured as a rigid support and protection structure for a flexible fluid bag. In one embodiment, the container housing includes a mechanism for expelling fluid from the bag contained therein. The invention may also comprise other features, such as a docking station or receptacle for the IV product and identification elements for the container housing and fluid bag associated therewith.

One embodiment of the invention will be described with reference to FIG. 2. As illustrated therein, an IV product 10 comprises a container housing 20 and a fluid bag or container 22. The container housing 20 may have a variety of shapes, sizes and configurations. In general, the container housing 20 is configured to support the fluid or IV bag 22. In one embodiment, as illustrated, the container housing 20 may generally house the fluid bag 22. As detailed below, the container housing 20 may be a relatively rigid structure which not only supports but also protects the fluid bag 22.

The fluid bag 22 preferably comprises a relatively flexible container for fluid, such as medication or the like. The fluid bag 22 may thus have a relatively thin wall construction.

Figure 2:
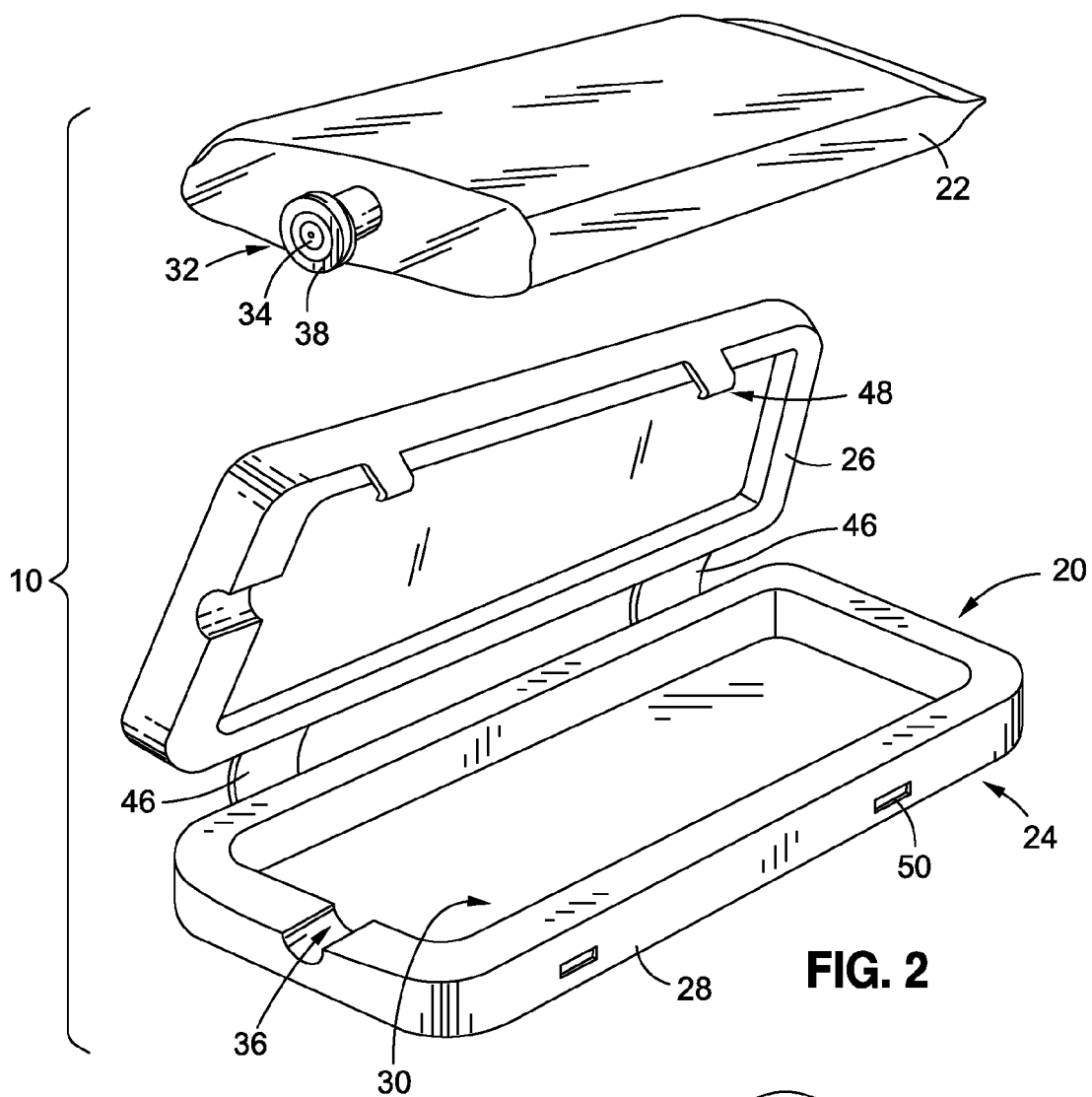
FIG. 2 illustrates an IV product in accordance with an embodiment of the invention, the product shown in an open/unassembled state.
Figure 3:
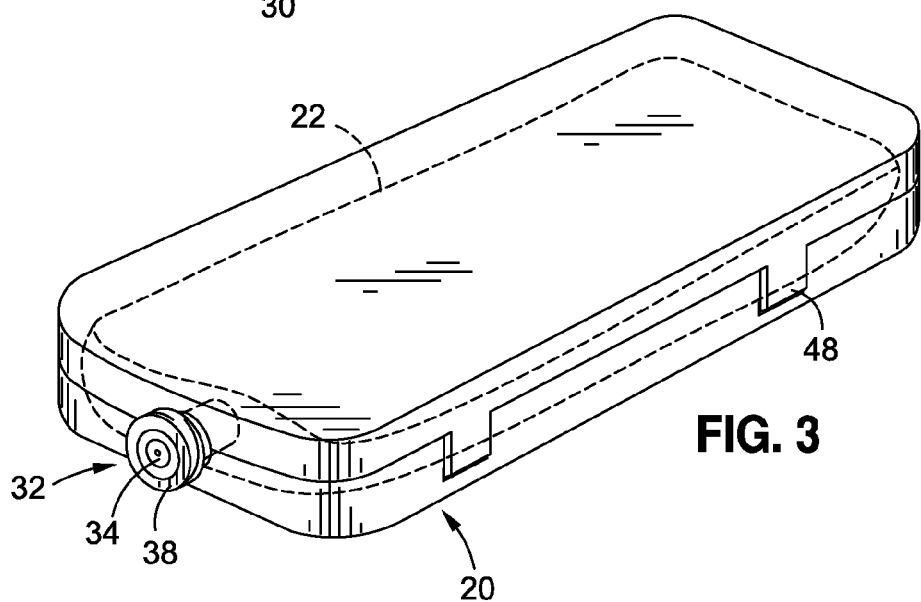
FIG. 3 illustrates the IV product in FIG. 2 in a closed/assembled state.

In one embodiment, as illustrated in FIGS. 2 and 3, the container housing 20 is configured as a body 24 defining an interior area for accepting, housing or containing the IV bag 22 therein. The body 24 may be constructed from a variety of materials and have a variety of shapes. In one embodiment, the body 24 has a top portion 26 and a bottom portion 28. The top and bottom portions 26,28 each have an exterior surface and an interior surface The interior surfaces may define concavities such that when the top and bottom portions 26, 28 are connected, the body 24 defines an interior area 30.

In one embodiment, as illustrated, the container housing 20 is generally rectangular in shape for accepting a correspondingly shaped fluid bag 22. It will be appreciated, however, that the container housing 20 (and fluid bag 22) might have a variety of other shapes (such as square, round, etc.).

The top and bottom portions 26,28 may be movable relative to one another to provide access to the interior area 30. For example, as illustrated in FIG. 2, the top and bottom portions 26,28 may be hingedly connected, thus permitting the top portion 26 to rotate from an open position to a closed position relative to the bottom portion 28. Of course, the top and bottom portions 26,28 might be moved between "open" and "closed" positions in other fashions, such as by having the top and bottom portions connectable in other fashions. In other embodiments, a portion of either the top and/or bottom may be openable or closeable. For example, the top portion 26 might have a door therein which can be opened to provide access to the interior area 30 of the container housing 20.

The container housing 20 might have other configurations. For example, the container housing 20 might be a relatively open structure, such as a webbed structure, or have a solid bottom portion but relatively open top portion.

The container housing 20 may be constructed of a variety of materials. For example, the container housing 20 might be molded from plastic or resin materials. The container housing 20 might be configured so that all or part thereof is transparent or opaque. The container housing 20 might be configured to be transparent, for example, to permit the fluid bag 22 therein to be easily viewed.

In one embodiment, the container housing 20 and fluid bag 22 are configured to provide a fluid connection. As illustrated in FIGS. 2 and 3, the fluid bag 22 is provided with at least one fluid connector 32. In one embodiment, this connector 32 comprises an extension of the body of the fluid bag 22 or a conduit or fluid path in communication therewith. The connector 32 may include a sealable fluid access, such as a no-drip needle-less connector. Such elements are well know in the art and may comprise a pierceable septum 34.

In one embodiment, the connector 32 may comprise a generally tubular member extending from the body of the fluid bag 22. The connector 32, or at least a portion thereof, may be relatively rigid. For example, a distal or end portion thereof may be relatively rigid while the proximal portion of the connector 32 at its connection to the fluid bag 22, may be flexible.

Preferably, the container housing 20 includes a fluid connector support. In one embodiment, the support 34 comprises a portion of the top and bottom portions 26,28 of the container housing 20. In one embodiment, the support 34 may be configured as an aperture 36 for accepting therein a portion of the fluid connector 32 of the fluid bag 22.

Preferably, the support 36 is configured to selectively capture and maintain the fluid connector 32 in a fixed position, such as for mating of the fluid bag 22 with a mating fluid connector or fluid delivery line, as detailed below. In one embodiment, to capture the fluid connector 32 and to prevent the fluid connector from sliding back into the interior 30 of the container housing 20, a flange 38 or other outwardly extending element may be provided on the fluid connector 32. The flange 38 is preferably sized to prevent the fluid connector 32 from moving backwardly through the support 36, as best illustrated in FIG. 3.

The support 36 may thus have a variety of configurations and features. For example, the support 36 might simply be an opening in the top or bottom portion 26,28 of the container housing 20 through which the fluid connector 32 may extend. In other embodiments, the support 36 might comprise a clip or other element for selectively engaging the fluid connector 32.

In one embodiment, the IV product 10 may include a means or mechanism configured to expel or deliver the contents of the fluid bag 22. In one embodiment, such a mechanism is configured to create a force or positive pressure upon the fluid bag 22, thus tending to force fluid from the fluid bag 22. As detailed, one embodiment of such a mechanism may be configured to reduce the volume of the interior space 30 within the container housing 20, thus reducing the space which may be occupied by the fluid bag 22.

Figure 4A:
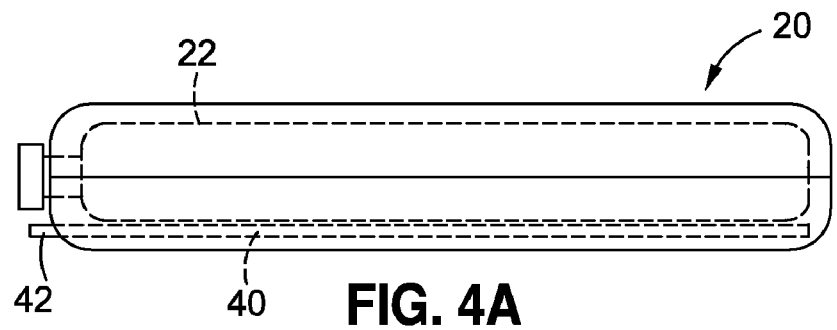
FIG. 4A illustrates another embodiment of an IV product in accordance with the invention, the product in a first condition.
Figure 4B:
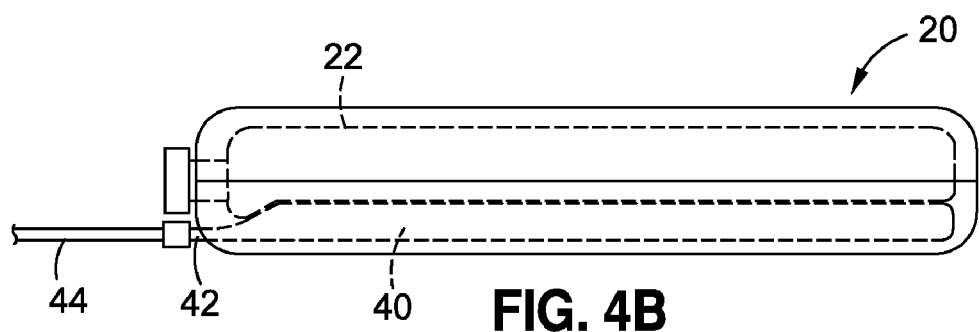
FIG. 4B illustrates the IV product in FIG. 4A in a second condition.

One embodiment of such an expelling mechanism is illustrated in FIGS. 4A and 4B. In a preferred embodiment, the mechanism comprises a member or members having a changeable size or volume. For example, as detailed below, in one embodiment, the mechanism may comprise a bellows 40 comprising a bag or body having a changeable volume. In one embodiment, the volume may be changed by changing a volume of fluid (such as air or liquid) within the bellows 40. In another embodiment, the mechanism may comprise one or more mechanical devices, such as a spring-driven body.

Referring to FIGS. 4A and 4B, the bellows 40 may comprise a bag which is located in the container housing 20. The bellows 40 preferably has an inlet 42 through which fluid may pass into and out of the bellows 40. In one embodiment, the container housing 20 may thus include an opening from the interior to the exterior thereof to provide access to the inlet 42 of the bellows 40.

In one embodiment, the bellows 40 may comprise a flexible bag, such as a rubber or plastic bag. A fluid delivery device, such as an air pump or the like, may be connected to the inlet 42 of the bellows 40, such as via an air line 44, thus providing fluid thereto. As will be appreciated, when fluid is delivered to the bellows 40, the fluid causes the bellows 40 to expand, as best illustrated in FIG. 4B. The bellows 40, in turn, compresses the fluid bag 22 in the container housing 20, tending to force fluid from the fluid bag 22 (when an appropriate fluid connection is provided to the fluid connector 32 of the fluid bag 22).

Of course, the expelling mechanism may have a variety of other configurations. For example, the bellows might be configured to be filled with liquid or air and liquid. In other embodiments, more than one bellows might be provided. In the embodiment illustrated, the bellows 40 is located below the fluid bag 22. However, the bellows 40 might be located above and/or below the fluid bag 22, or might be located at one or both ends of the fluid bag 22. Also, more than one bellows 40 might be provided.

As indicated, other types of mechanisms might be provided for expelling fluid from the fluid bag 22. For example, the mechanism might comprise a movable platform located in the interior 30 of the container housing 20. The mechanism might include a biasing member, such as one or more springs, for moving the platform inwardly to compress the fluid bag 22.

In order to maintain the container housing 20 in a closed position, such as when the expelling mechanism is activated and a force is being generated in the interior 30 thereof, the top and bottom portions 26,28 may be secured to one another. As illustrated in FIGS. 2 and 3, the top and bottom portions 26,28 may be connected by one or more elements 46, such as hinges, at one portion or side thereof. In one embodiment, the hinges 46 may comprise flexible portions of material which are connected to both the top and bottom portions 26,28 of the container housing 20. In other embodiments, the hinges 46 might comprise two or more members which are configured to move relative to one another, one of which is connected to the top portion 26 and the other of which is connected to the bottom portion 28 of the container housing 20.

One or more latches 48 may be provided for connecting opposing or other portions of the container housing 20. In one embodiment, each latch 48 be associated with the top portion 26 of the container housing 20 and be configured to selectively engage the bottom portion 28 of the container housing 20.

In the illustrated embodiment, each latch 48 is movably or hingedly connected to the top portion 26 of the container housing 20. The latch 48 has a tab (not visible) for selective engagement with the bottom portion 28 of the container housing 20, such as a slot or notch 50 therein. When engaged, each latch 48 pulls the top portion 26 and bottom portion 28 towards one another.

In one embodiment, there may be more than one latch 48, such as two or more. Also, the latch 48 or other securing mechanism may have other configurations. For example, the latch might comprise a rotating catch, might include one or more threaded members or the like.

In one embodiment, the top and bottom portions 26,28 of the container housing 20 may be sealable so as to provide a sealed interior space 30. In such a configuration, air or other fluid might be input directly into the interior of the container housing 20. As the pressure of this fluid increases, the fluid bag 22 is compressed, expelling the contents of the bag 22. In other embodiments, it is possible to inject air directly into the fluid bag 22 in order to force the fluid therefrom, or force air or other fluid into a chamber or bellows formed with or in the fluid bag 22.

Figure 5:
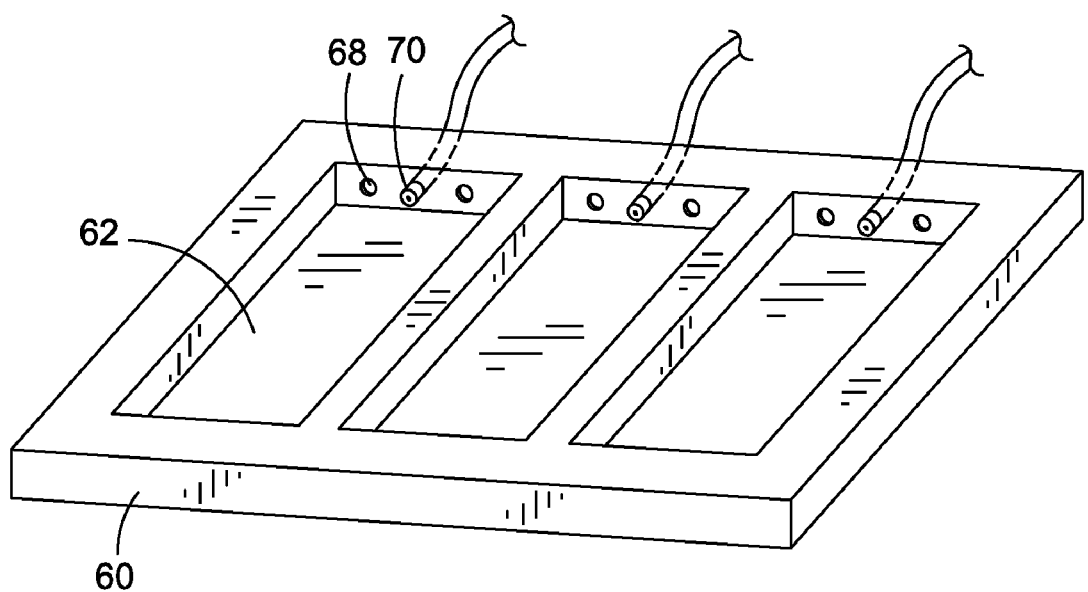
FIG. 5 illustrates a docking station or receptacle for an IV product.

In one embodiment of the invention, as illustrated in FIG. 5, the IV product of the invention may be configured to engage a docking station or receptacle 60 or otherwise be connected to one or more other devices or elements. For example, in one embodiment, a docking station 60 may comprise or define one or more ports 62 for one or more corresponding IV products. The ports 62 might comprise recessed areas in a body or structure, into which a container housing may be located. In other embodiments, the ports may simply comprise fluid connectors or connections for mating connection to the fluid connector 32 of the fluid bag 22. There may be as few as one, or two or more ports 62 associated with the docking station 60.

Figure 6:
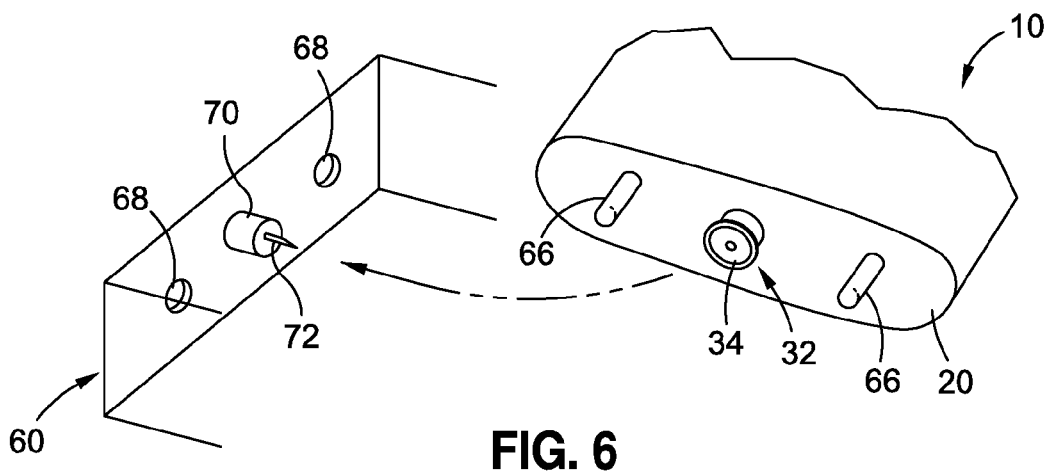
FIG. 6 illustrates a connector configuration for an IV product and docking station.

In one embodiment, one or more connectors or other members may be provided for mating the container housing 20 to a port 62 of the docking station 60 or another element. For example, referring to FIG. 6, the container housing 20 may include at least one element for mating engagement with the docking station 60 or an element thereof.

As illustrated, one or more pins 66 may extend outwardly from the container housing 20. In one embodiment, a pair of pins 66 may extend outwardly from an end of the container housing 20. These pins 66 may be configured to engage mating apertures 68 of the docking station 60.

In one embodiment, when the container housing 20 and associated fluid bag 22 are connected to the docking station 60, a fluid connection is preferably provided to the fluid bag 22. As illustrated, a mating fluid connector 70 is preferably provided at each port 62 for mating with the fluid connector 32 of the fluid bag 22.

In an embodiment where the fluid connector 32 of the fluid bag 22 comprises a pierceable septum, the port fluid connector 70 may comprise a needle 72 or similar piercing member. The needle 72 may be inset into the docking station 60 or a shroud or the like so as to prevent accidental needle-sticks.

Preferably, the container housing 20 is moved into engagement with the docking station 60 at a port 62 thereof. The container housing 20 is aligned with the docking station 60, such as by extending the pins 66 into the mating apertures 68 in the docking station 60. As this occurs, a fluid connection is preferably established between the docking station 60 and the fluid bag 22, such as by the needle 72 piercing the septum 34 of the fluid bag 22.

Of course, a wide variety of other elements may be utilized to accomplish the purpose of aligning and/or connecting the connector housing 20/fluid bag 22 with the other member. For example, IV product might be aligned with a mating fluid connector as a result of the shape of the inset or port of the docking station, whereby the container housing 20 fits tightly within the inset or port. Other types of locking or connecting elements might be used in addition to or separately from such an alignment mechanism, such as the disclosed pin(s). Preferably, these elements include at least one member or element of the container housing 20 or associated with the container housing 20 for selectively engagement with an external component, such as a port, dock, pump or the like. In this regard, it will be appreciated that the container housing 20 and associated fluid bag 22 may be configured to engage other than a docking station 60. For example, the IV product of the invention could be configured to directly engage a fluid pump or the like.

As indicated above, in one embodiment, an expelling mechanism is provided to aid in expelling fluid from a fluid bag 22 associated with the container housing 20. In one embodiment, that mechanism may be associated with another device, such as the docking station 60 or port to which the IV product may be coupled. In one embodiment, when the container housing 20 is mated to a docking port, a fluid connection may be established with the fluid bag 22 and a fluid connection may be established with the interior 30 of the container housing 20 or with the bellows, thus allowing fluid to be introduced therein. In another embodiment, the external device may include means for compressing the fluid bag 22, such as a movable plate or the like.

Figure 7:
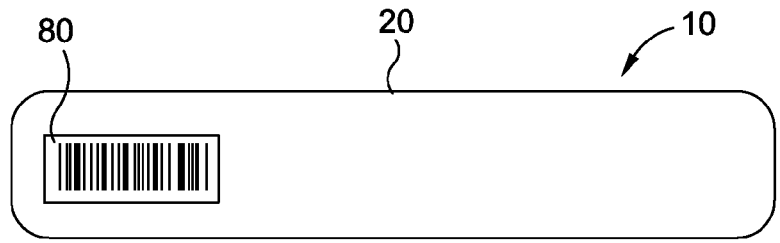
FIG. 7 illustrates an IV product of the invention bearing an information element.

As illustrated in FIG. 7, the IV product 10 may be provided with information, such as an information element 80. In a preferred embodiment, the information element 80 is associated with the container housing 20. The information element 80 may, however, be associated with the fluid bag 22. In such instance, the container housing 20 may be configured to allow the information element 80 to be visible, such as by having port or window aligned therewith or having portion thereof be transparent so that the information element may be read through the container housing 20. The information element 80 may comprise printing, such as a 2 or 3-D bar code, text or symbols or combinations thereof. For example, in the embodiment illustrated in FIG. 7, the information element 80 comprises a printed bar code. The information element might 80 might also comprise an RFID tag, magnetic stripe, microchip (such as a chip located on the container, the chip having a connector for connection to a reader located at a docking station or other device), memory device or other electronic information storage device or the like.

The information element 80 may be configured to comprise or identify a variety of information. For example, the information element 80 may identify a file of information, or itself provide specific information. This information might identify, for example, the fluid which is located in the fluid bag 22, the patient for which the fluid is intended, the source of the fluid bag (such as manufacturer), expiration date, product size or volume, doctor, hospital, pharmacy, or a wide range of other information.

Figure 8:
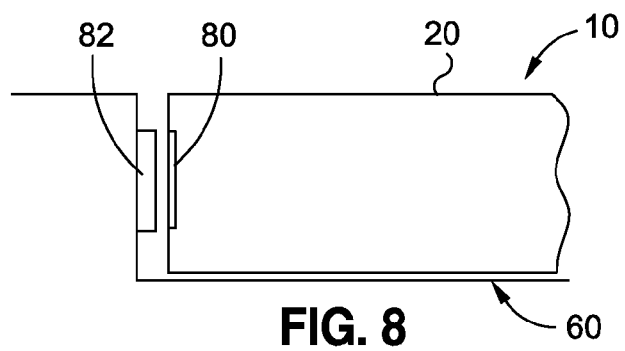
FIG. 8 illustrates an information reader for reading an IV product information element.

As illustrated in FIG. 8, a reader 82 may be provided for reading the information associated with the IV container, such as the information element 80. The reader 82 may comprise one or more of a variety of devices configured to read, capture or otherwise receive information. For example, the reader 82 might comprise an optical scanner for reading printed text, a bar code or the like. The reader 82 might comprise a magnetic stripe reader for reading magnetically encoded information.

In one embodiment, as illustrated in FIG. 8, the reader 82 may be associated with the docking station 60 or other IV product receptacle. Preferably, the reader 82 is situated or oriented to read the information associated with the IV container when the container 20 is associated with the docking station 60. Thus, in one configuration, a reader 82 is preferably associated with each of the ports 62 of the docking station 60. For example, a reader 82 may be provided at an end of each of the ports 62 for reading the information element 80 at the end of the container 20, as illustrated in FIG. 8.

Of course, a reader 80 may be associated with other elements or devices. For example, if the IV container is to be associated with an infusion pump, the reader could be associated directly with the pump.

Figure 9:
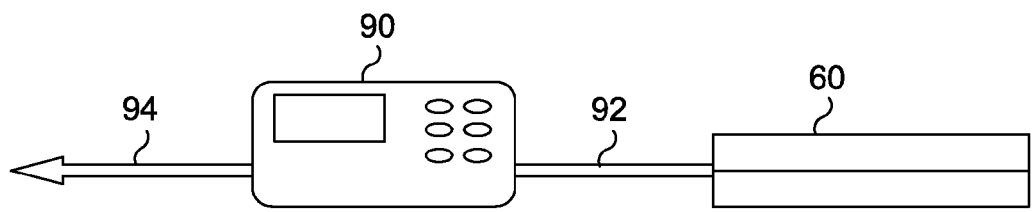
FIG. 9 illustrates a docking station coupled to an infusion pump for delivering fluid from an IV product of the invention.

One configuration of a system applicable to the IV product of the invention is illustrated in FIG. 9. As illustrated, a docking station 60 may be associated with an infusion pump 90. As detailed above and illustrated in FIG. 5, the docking station 60 may be configured to receive one or more IV products. Preferably, when an IV product is associated with the docking station 60, a fluid connection is established with the IV product.

As illustrated, one or more fluid lines 92 may be provided between the docking station 60 or other receptacle and the infusion pump 90. The infusion pump 90 may be configured to deliver fluid to one or more delivery lines 94, such as a fluid line leading to a patient.

Use of the IV product of the invention and various additional aspects of the invention will now be described.

Figure 1:
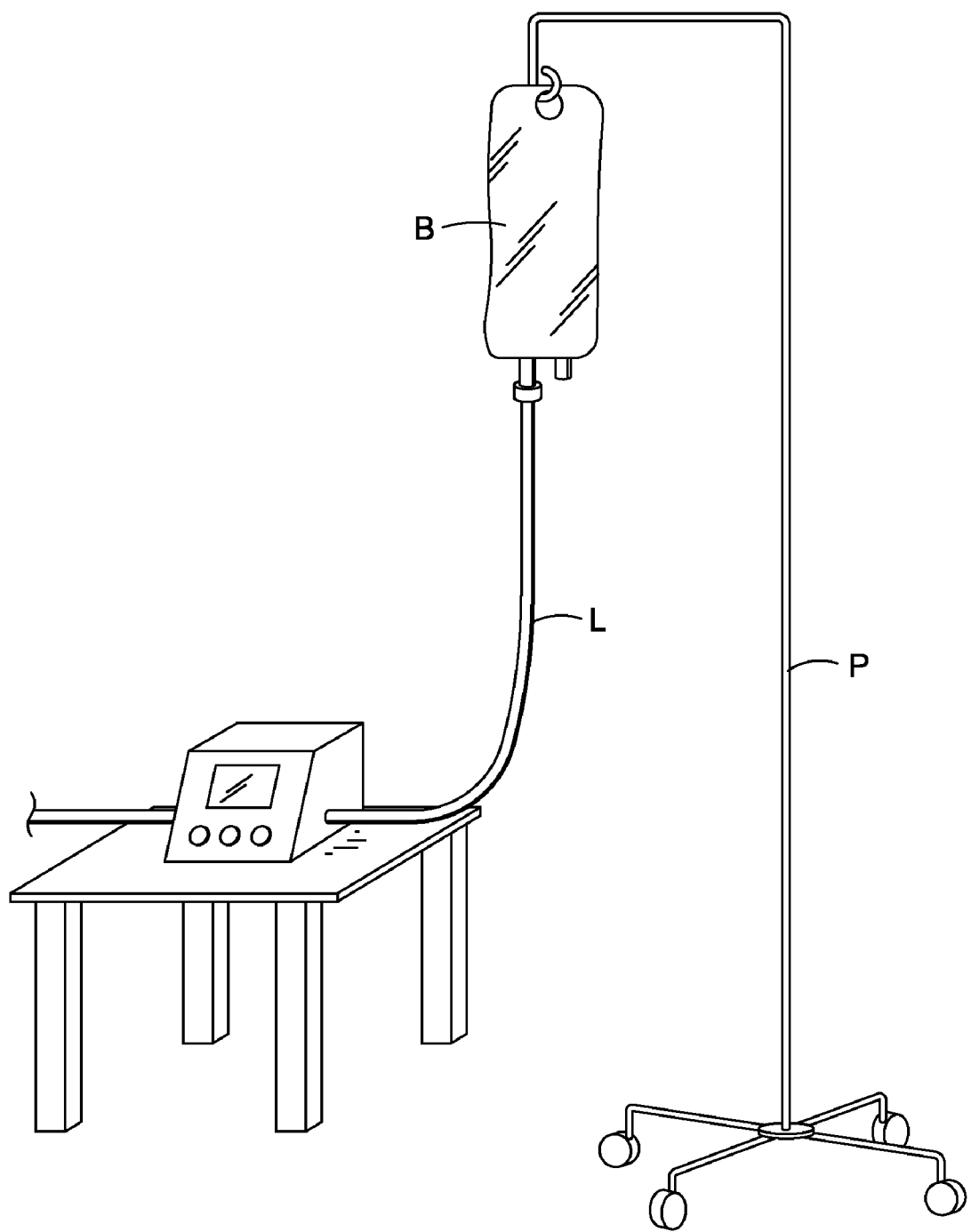
FIG. 1 illustrates an IV bag and delivery method in accordance with the prior art.

First, the IV product of the invention is prepared. This could comprise filling the fluid bag 22 with appropriate fluid (such as medication, saline, etc.). In an embodiment in which the fluid bag 22 and container housing 20 are separated or separable, the fluid bag 22 may then be associated with a container housing 20. For example, as indicated above, this may comprise opening the container housing 20 and inserting the fluid bag 22 therein. In the embodiment illustrated in FIG. 1, the top portion 26 of the container housing 20 may be opened relative to the bottom portion 28, thereby providing access to the interior area 30. After the fluid bag 22 is inserted, the top portion 26 may be closed relative to the bottom portion 28 to trap or contain the fluid bag 22. In the embodiment illustrated, the latches 48 may be latched to secure the fluid bag 22 in the container housing 20. In an embodiment in which the fluid bag 22 and container housing 20 are integrated (such as being designed for a single use), the fluid bag 22 may be filled while associated with the container housing 20.

In order to secure the fluid bag 22 in position, the fluid connector 32 of the fluid bag 22 is preferably extended through the support 36. The flange 38 of the fluid connector 32 is located outside of the container housing 20.

Information is preferably associated with the IV product, such as the container housing 20. As indicated, the information may vary. For example, if the fluid bag 22 is prepared with particular medication for a particular patient, the information may include such. In one embodiment, such information may be input into a database and a printer may generate a barcode corresponding to the information. The barcode may, for example, be printed on an adhesive label which is affixed to the container housing 20.

In use, the IV product is connected to a fluid delivery device. In one embodiment, the container housing 20 is connected to a receptacle, such as the docking station 60 illustrated in FIG. 5. If the receptacle or docking station 60 has no open ports, a used/depleted product may be removed and the new container inserted in its place. If the receptacle or docking station 60 has one or more additional or open ports 62, the container 60 may be inserted into an open port 62.

Preferably, the IV product is associated with the receptacle so that a fluid connection is established with the fluid bag 22. For example, in the embodiment illustrated in FIG. 6, the container housing 20 is preferably inserted so that the pins 66 fit within the corresponding apertures 68 of the port 66. When fully inserted, the needle 72 of the fluid connector 70 of the docking station 60 preferably penetrates the septum 32 of the fluid connector 32 of the fluid bag 22.

In one embodiment, the fluid bag 22 may be located in a position at which gravity, an associated fluid pump or the like is sufficient to cause fluid to be delivered from the fluid bag 22. In other situations, such as where the fluid bag 22 is at a level at which gravity or a fluid pump do not deliver fluid (or deliver it at sufficient rates), the fluid may be expelled from the bag by application of force. With reference to the embodiment illustrated in FIGS. 4A and 4B, air or other fluid may be delivered to the bellows 40, thus causing the bellows to expand, causing fluid to be expelled from the fluid bag 22. Of course, the method by which the fluid is expelled may vary depending upon the expelling mechanism, as detailed above.

Preferably, when the IV product is utilized, the information associated therewith is read and that information is utilized. In the embodiment illustrated in FIG. 8, the information element 80 is read by the reader 82 when the container housing 20 is inserted into the port 62 of the docking station 60. In one embodiment, the reader 82 (and/or an external computing device) is configured to decode the information (such as the bar code) or to utilize the information to obtain information (for example, the information on the container housing 20 may identify a file or account containing information, such as located at a remote server).

The information may be utilized in the use of the IV product. For example, the information may be utilized by an infusion pump to control the flow rate of fluid to a patient. Referring to FIG. 9, for example, the reader may send control information from the docking station 60 to the infusion pump 90. The information might also be utilized to verify that the correct medication is being provided to a patient, that the fluid is intended for the particular patient, or a wide range of other purposes.

As indicated, in one embodiment of the invention, the container housing and fluid bag are separable elements. In other embodiments, they may be inseparable. For example, the fluid bag may be formed with or securely connected to the housing. In the case where the container housing and fluid bag are separable, a used fluid bag might be discarded and the container housing re-used with a new fluid bag. In the case where they are inseparable, the entire unit may be discarded upon use.

As indicated, the container housing may be generally enclosed or event sealed, or it might be an open frame or other support structure. The container housing may include additional features such as mounts or connections, such as to permit the container housing to be stored or picked up, such as with mechanical elements. For example, the container housing might include locating holes, slots, pins or the like for connection to a mounting rack or other structures or devices.

The fluid bag may be a single layer of material or may be multi-layer. The fluid bag may also be opaque, transparent, colored, conductive, non-conductive or have other properties.

As indicated, in one embodiment a mechanism may be provided for expelling fluid from the fluid bag. In one embodiment, the IV product may include a flow sensor and/or a volume sensor. The flow and/or volume sensor may provide feedback, such as to the expelling mechanism so as to provide a controlled fluid flow delivery rate from the fluid bag, and/or provide information regarding the amount of fluid delivered or amount of fluid remaining in the bag. For example, when the bag is nearly empty (as estimated by flow rate determination or directly by the volume sensor) a warning signal may be generated.

In one embodiment, container housings and docking ports or receptacles may have different configuration to permit only certain IV products to be mated with certain ports, receptacles or other devices. For example, the pattern of the pins extending from the container housing may vary, as may the corresponding aperture patterns of the ports. In this manner, for example, certain IV products might be usable only with certain ports, receptacles or other device. Such might be used to reduce the accidental connection of an IV product, and thus undesired delivery of fluid.

In one embodiment, the docking station or other receptacle or device may include a flow controller or other means for ensuring that fluid is not delivered from the fluid bag until or unless there is verification of the IV product. For example, the reader may be required to read information from the IV product and verify the information before a signal is transmitted to the flow controller to permit fluid to be delivered from the bag. In one embodiment, the reader may read the information and that information might be compared to master patient, prescription and scheduling information to verify that the IV product is meant for that patient, it is the correct time and the correct fluid to be provided to the patient.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. An intravenous (IV) product comprising:
a housing configured to engage a docking station of an IV pump;
a flexible fluid bag disposed within the housing, said bag configured to contain a medical fluid and comprising at least one fluid connector configured to fluidically connect with a mating fluid connector of the docking station as the housing is engaged with the docking station;
at least one alignment feature coupled to the housing, the alignment feature configured to engage a matching alignment element of the docking station such that the IV product will not engage the docking station in the absence of one of the alignment feature and alignment element, wherein connection is established between the at least one fluid connector and the mating fluid connector only after the alignment feature engages the matching alignment element; and
a machine-readable information element coupled to the housing, the information element configured to mate with a reader of the docking station as the housing is engaged with the docking station, the information element further configured to store and provide at least an identifier associated with the IV product.

2. The IV product of claim 1, wherein:
the docking station comprises a recessed area in the IV pump;
the housing is configured to engage the docking station by being located into the recessed area; and
the connection between the at least one fluid connector and the mating fluid connector is established only after the housing is at least partially located within the recessed area.

3. The IV product of claim 1, wherein said information element comprises information printed on said housing.

4. The IV product of claim 1, wherein said information element comprises an information-storing electronic device, wherein the information element is configured to mate with an electrical connector coupled to the reader as the housing is engaged with the docking station.

5. The IV product of claim 4, wherein the information element comprises at least one of the set of an identification of the fluid contained in the fluid bag, an expiration date, and expiration time.

6. The IV product of claim 4, wherein the information element comprises an identification of a patient for whom the fluid is intended.

7. The IV product of claim 1, wherein said housing comprises a top portion and bottom portion defining an interior volume in which said fluid bag is located.

8. The IV product of claim 1, further comprising an expelling mechanism.

9. The IV product of claim 8, wherein said expelling mechanism comprises a bellows supported by said housing.

10. The IV product of claim 9, wherein said bellows comprises a flexible membrane having at least one inlet through which fluid may be introduced to said bellows.

11. The IV product of claim 1, wherein said housing is sealed, permitting internal pressurization of a space between the housing and the fluid bag disposed therein.

12. An IV pumping system, the system comprising:
an IV pump comprising:
- a docking station;
- an alignment element coupled to the docking station;
- a fluid connector coupled to the docking station; and
- a reader coupled to the docking station; and an IV product comprising:
- a housing configured to engage the docking station;
- a flexible fluid bag disposed within the housing, said bag configured to contain a medical fluid and comprising at least one fluid connector configured to fluidically connect with the fluid connector of the docking station as the housing is engaged with the docking station;
- at least one alignment feature coupled to the housing, the alignment feature configured to mate with the alignment element of the docking station such that the IV product will not engage the docking station in the absence of one of the alignment feature and alignment element, wherein connection is established between the at least one fluid connector and the fluid connector of the docking station only after the alignment feature mates with the alignment element; and
- a machine-readable information element coupled to the housing, the information element configured to mate with the reader of the docking station as the housing is engaged with the docking station, the information element further configured to provide information comprising at least an identifier.

13. The system of claim 12, wherein said container housing comprises a top portion and a bottom portion defining an interior volume in which said fluid bag is located.

14. The system of claim 12, wherein:
- a first set of IV products are configured with a first alignment feature;
- at least one second set of IV products are configured with a second alignment feature that is different from the first alignment feature;
- the alignment element of the IV pump is configured to mate with the first alignment feature and thereby permit the first set of IV products to engage the docking station; and
- the alignment element of the IV pump is further configured to not mate with the second alignment feature and thereby prevent the at least one second set of IV products from engaging the docking station.

15. The system of with claim 14, wherein:
- the IV pump comprises a plurality of docking stations; and
- the IV pump comprises a plurality of alignment elements respectively associated with the plurality of docking stations, each of the plurality of alignment elements configured to mate with the alignment features of at least one set of IV products and to not mate with the alignment features of at least one other set of IV products.

16. The system of claim 12, wherein said expelling mechanism comprises an inflatable bellows.

17. The system of claim 12, wherein the IV pump further comprises a flow controller configured to ensure that fluid is not delivered from the flexible fluid bag until the information read from the information element is compared by the IV pump to patient information previously entered into the IV pump to verify that the IV product is meant for the patient.

* * * * *